US011051691B2

(12) United States Patent
Gunnerson et al.

(10) Patent No.: US 11,051,691 B2
(45) Date of Patent: Jul. 6, 2021

(54) OCULAR ANALYSIS

(71) Applicant: VYE, LLC, Dayton, OH (US)

(72) Inventors: Kory Adam Gunnerson, Cincinnati, OH (US); Jordan Doczy, Oakwood, OH (US); Joshua M. Gratsch, Brookville, OH (US); Maria Lupp, Dayton, OH (US)

(73) Assignee: VYE, LLC, Dayton, OH (US)

( * ) Notice: Subject to any disclaimer, the term of this patent is extended or adjusted under 35 U.S.C. 154(b) by 329 days.

(21) Appl. No.: 16/050,326

(22) Filed: Jul. 31, 2018

(65) Prior Publication Data
US 2019/0029513 A1    Jan. 31, 2019

Related U.S. Application Data

(60) Provisional application No. 62/539,234, filed on Jul. 31, 2017.

(51) Int. Cl.
| A61B 3/113 | (2006.01) |
| A61B 5/11  | (2006.01) |
| A61B 3/02  | (2006.01) |
| A61B 5/00  | (2006.01) |

(52) U.S. Cl.
CPC .............. *A61B 3/113* (2013.01); *A61B 3/02* (2013.01); *A61B 5/11* (2013.01); *A61B 5/4064* (2013.01)

(58) Field of Classification Search
CPC .. A61B 3/113; A61B 3/02; A61B 5/11; A61B 5/4064
USPC ......................................................... 351/209
See application file for complete search history.

(56) References Cited

U.S. PATENT DOCUMENTS

| 8,950,864 | B1  | 2/2015  | Massengill |
| 2007/0032737 | A1 | 2/2007  | Causevic et al. |
| 2008/0208073 | A1 | 8/2008  | Causevic |
| 2012/0330178 | A1 | 12/2012 | Kraft et al. |
| 2017/0124699 | A1 | 5/2017  | Lane |
| 2017/0311799 | A1* | 11/2017 | Holt .................... A61B 5/4064 |

(Continued)

OTHER PUBLICATIONS

Enright, J.T.; "Estimating peak velocity of rapid eye movements from video recordings"; Behavior Research Methods, Instruments, & Computers; 1998.

(Continued)

*Primary Examiner* — Marin Pichler
*Assistant Examiner* — Mitchell T Oestreich
(74) *Attorney, Agent, or Firm* — Thomas E. Lees, LLC

(57) ABSTRACT

A process for ocular analysis is disclosed. Aspects of the process display, on a device having a display and a camera sensor, a regimented pattern as a stimulus. The camera sensor captures video of an environment. The process also involves isolating an iris within the environment as a bounded region of the captured video. Facial landmarks are assigned to the iris within the bounded region. Thereafter, raw movement data of the facial landmark in response to the regimented pattern is extracted from the captured video. The raw movement data is used to create filtered movement data (e.g., data that has been checked for errors). The process also compares the filtered movement data to a predetermined movement response that is based on the regimented pattern. From the comparison, a performance score is generated. The performance score is used to generate an output.

10 Claims, 14 Drawing Sheets

(56) References Cited

U.S. PATENT DOCUMENTS

2017/0354369 A1 12/2017 Mills
2018/0121608 A1 5/2018 Gross et al.

OTHER PUBLICATIONS

Logan, S.; Concussion Treatment: Convergency Insufficiency; MikeReinold.com; https://mikereinold.com/concussion-treatment-convergence-insufficiency/; 2017.
Wong, A.; "Eye Movement Disorders"; Part I The Six Eye Movement Systems; Functions and Characteristics of Saccades; Oxford University Press; 2008.
Apple Inc.; "HitCheck: Concussion Test; Sideline assessment & recovery; Handheld Head Injury Treatment Tool"; App Store Preview; 2016.
Brooke de Lench; "Concussion Apps for Smartphones"; momsTEAM; Nov. 12, 2013.
Saccadous; "Diagnosing Sports Concussions: There's an App for That"; Feb. 1, 2016.
Nick Lavars; "Smartphone app scans pupils to detect concussions"; New Atlas; Sep. 7, 2017.
Kurtis Sluss; "Detect a Concussion in Seconds—App by brightlamp"; Indiegogo; downloaded on Sep. 13, 2019 at https://www.indiegogo.com+/projects/detect-a-concussion-in-seconds-app-by-brightlamp-smartphone-application#/.
Lizette Borreli; "This New App Detects Concussions Just by Looking Into Your Eyes"; Newsweek; Sep. 11, 2017.

\* cited by examiner

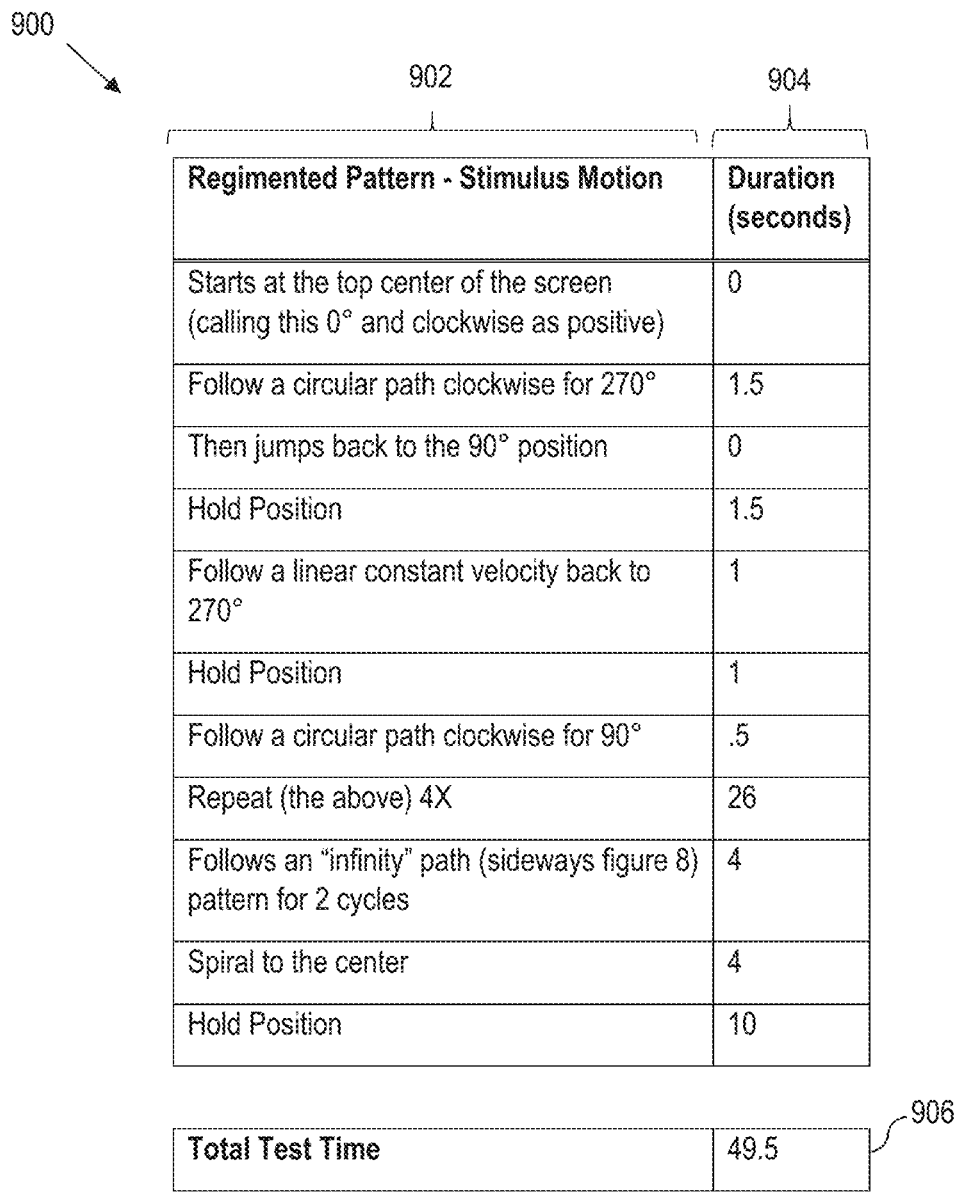

| Regimented Pattern - Stimulus Motion | Duration (seconds) |
|---|---|
| Starts at the top center of the screen (calling this 0° and clockwise as positive) | 0 |
| Follow a circular path clockwise for 270° | 1.5 |
| Then jumps back to the 90° position | 0 |
| Hold Position | 1.5 |
| Follow a linear constant velocity back to 270° | 1 |
| Hold Position | 1 |
| Follow a circular path clockwise for 90° | .5 |
| Repeat (the above) 4X | 26 |
| Follows an "infinity" path (sideways figure 8) pattern for 2 cycles | 4 |
| Spiral to the center | 4 |
| Hold Position | 10 |

| Total Test Time | 49.5 |
|---|---|

FIG. 9

| TEST | METRICS / MEASUREMENTS | | CAUSE OF DISRUPTION OF THE BRAIN | | | | | |
|---|---|---|---|---|---|---|---|---|
| | | | mDBI | OPIOID USE | MARIJUANA USE | INTOX | PARK | ALZ |
| SACCADE | LATENCY | ms | 60% | 60% | 40% | 60% | | |
| | ACCURACY | % | 10% | | | | 80% | |
| | VELOCITY | deg/sec | | 40% | | | | |
| SELF-PACED SACCADE | REFIXATIONS | COUNT | 60% | | 75% | | | 80% |
| | INTERSACCADIC INTERVAL | ms | 80% | | | | | |
| SMOOTH PURSUIT | GAIN VELOCITY | % | 50% | 80% | | | | |
| | ACCURACY | deg | | | | | | |
| GAZE | STABILITY | deg | 40% | | 75% | | | 60% |
| | ACCURACY | deg | | | | | | |
| NYSTAGMUS | PRESENCE | Y/N | 30% | | | 80% | | |
| | FREQUENCY | COUNT | | | | 60% | | |
| | AMPLITUDE | deg | | | 20% | | 15% | |
| VERGENCE | MINIMUM ACCOMMODATION DISTANCE | cm | 80% | | | 20% | 45% | |
| PUPIL RESPONSE | PUPIL SIZE | % | | 25% | 25% | | | |
| | LATENCY | ms | 40% | 60% | 40% | 55% | | |
| | CONSTRICTION RATE | %/sec | | | 30% | | | |
| ACCOMMODATION | ACCOMMODATIONS | COUNT | 35% | 60% | 40% | | 20% | 45% |
| | ACCOMMODATION RATE | ms/sec | 20% | | | | | |
| COGNITIVE ASSESSMENT | QUESTION SCORE | COUNT | 80% | 80% | 60% | 60% | | 60% |
| NEUROLOGICAL ASSESSMENT | TESTING SCORE | COUNT | 30% | 60% | | 45% | 80% | |

OCULAR ANALYSIS

CROSS-REFERENCE TO RELATED APPLICATIONS

This application claims the benefit of U.S. Provisional Patent Application Ser. No. 62/539,234, filed Jul. 31, 2017, entitled "OCULAR MOTOR ANALYSIS ON A MOBILE PLATFORM", the disclosure of which is hereby incorporated by reference.

BACKGROUND

Various aspects of the present disclosure relate generally to ocular analysis, and more specifically to ocular analysis for determining brain function.

Traumatic brain injuries (TBI) can be the result of blunt trauma to the head, a stroke, or some other neurological dysfunction. Symptoms of TBI vary from person to person, but may include blurred vision sensitivity to light, glare sensitivity, reading difficulties, words appearing to move, comprehension difficulty, attention and concentration difficulty, memory difficulty, double vision, aching eyes, and headaches with visual tasks.

BRIEF SUMMARY

According to aspects of the present disclosure a process for ocular analysis is disclosed. Aspects of the process display, on a device having a display and a camera sensor, a regimented pattern as a stimulus. The camera sensor captures video of an environment. The process also involves isolating an iris within the environment as a bounded region of the captured video. Facial landmarks are assigned to the iris within the bounded region. Thereafter, raw movement data of the facial landmark in response to the regimented pattern is extracted from the captured video. The raw movement data is used to create filtered movement data (e.g., data that has been checked for errors). The process also compares the filtered movement data to a predetermined movement response that is based on the regimented pattern. From the comparison, a performance score is generated. The performance score is used to generate an output.

According to aspects of the present disclosure a system for ocular analysis is disclosed. The system uses a device comprising a processor coupled to memory, a camera sensor, a storage medium, and a display. A program in the memory instructs the processor to perform various actions including instructions to display a regimented pattern as a stimulus on the display. The program also instructs the processor to capture video of an environment via the camera sensor. Using the camera sensor, the program further instructs the processor to isolate an iris within the environment as a bounded region of the captured video. Facial landmarks are assigned to the iris within the bounded region. Thereafter, the program instructs the processor to extract raw movement data of the facial landmark in response to the regimented pattern. The raw movement data is used to create filtered movement data (e.g., data that has been checked for errors). The filtered movement data is compared to a predetermined movement response that is based on the regimented pattern. From the comparison, a performance score is generated. The performance score is used to generate an output.

BRIEF DESCRIPTION OF THE SEVERAL VIEWS OF THE DRAWINGS

FIG. 9 illustrates an example ocular test according to various aspects of the present disclosure as described in greater detail herein;

FIG. 12 is a table illustrating example probabilities between test metrics and disruption in normal brain function according to various aspects of the present disclosure as described in greater detail herein;

DETAILED DESCRIPTION

Traumatic brain injuries (TBI) and other disruptions of normal brain function (DNBF) (collectively hereinafter "brain injury") can have profound health consequences if the brain injury is not identified or addressed. While signs and symptoms of brain injury vary from person to person, ocular motor functions can provide an indication as to whether a brain injury is present. Accordingly, aspects of the present disclosure are directed toward ocular analysis processes and systems.

Aspects of the present disclosure present a regimented pattern to a test subject. As the regimented pattern takes place, the test subject's eyes are tracked (e.g., tracking the eyes via the iris) by a camera sensor. Rather than simply generating an output based on the tracked eye movement, as may be the case with some previous solutions, aspects of the present disclosure further create filtered movement data, which is data where erroneous or bad data has been removed. Further, regions of interest within the filtered movement data are analyzed to generate a performance score, which may be indicative of a brain injury.

Some previous solutions for identifying brain injury through ocular analysis have relied on analysis of the pupil of the eye. For example, such previous solutions use a camera flash to cause a reaction in the pupil. Generally, a flash of light will cause of the pupil to contract. Once the camera flash is gone, the pupil tends to dilate back into a normal state. The previous solutions measure various aspects of the pupil as it contracts and dilates to determine a likelihood of some sort of neurological dysfunction.

One advantage to the above aspects of the present disclosure is that less data needs to be processed than the existing solutions, which results in generating faster results when compared to the existing solutions, thus improving the technology of data processing and diagnostics. Moreover, during creation of the filtered movement data, erroneous data may be identified and discarded from consideration when generating the performance score, which may result in a higher confidence level in the analysis. Further benefits and advantages associated with aspects of the present disclosure are detailed below.

Ocular Analysis Process

Figure 1:
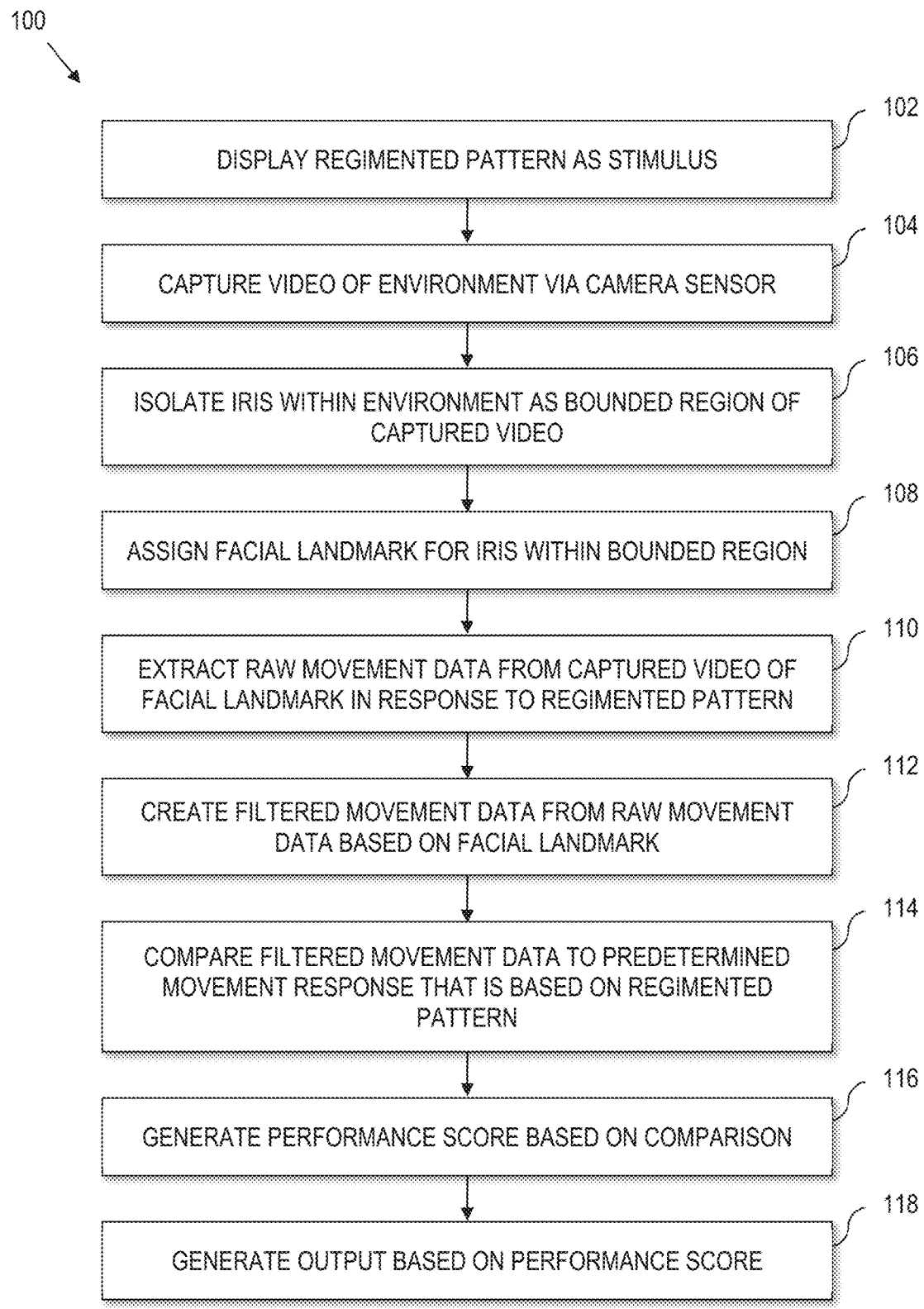
FIG. 1 is a flow chart of a process for ocular analysis according to various aspects of the present disclosure as described in greater detail herein.

Referring to drawings and in particular FIG. 1, a process 100 for ocular analysis is illustrated. The process 100 comprises displaying at 102, on a device having a display and a camera sensor, a regimented pattern as a stimulus. The regimented pattern is discussed in greater detail below.

Still referring to FIG. 1, the process 100 further comprises capturing at 104 video of an environment via the camera sensor. The captured video is not limited to any specific resolution, frame rate, or format (e.g., audio video interleave (AVI), video object (VOB), etc.). Similar to the stimulus, as noted above, the captured video can be fixed or variable in terms of frame rate. In various embodiments, the process 100 synchronizes a frame rate of the camera sensor with a frame rate of the stimulus (i.e., regimented pattern) as the video is captured (i.e., the frame rates are synchronized).

Moreover, in various embodiments captured video can be stored on any suitable storage medium. For example, captured video may be stored on the device itself, stored in a remote location, or both as described in greater detail herein.

The process 100 also comprises isolating, at 106, an iris or an eye within the environment as a bounded region of the captured video.

Further, the process 100 comprises assigning, at 108, a facial landmark for an iris within the bounded region. Facial landmarks may be conceptualized as virtual points or markers that are assigned to specific parts of the iris. Further, in various embodiments assigning the facial landmark(s) may further comprise a reference point within the bounded region. One example of a reference point is a fiducial marker.

Generally, a fiducial marker (or "fiducial") is an object placed in a field of view of an imaging system which appears in the image produced, for use as a point of reference or a measure. For example, the fiducial marker may be either something placed into or on the imaging subject or a mark (or set of marks) in a reticle of an optical instrument such as a camera sensor.

In some embodiments, a set of facial landmarks may be assigned. For example, in embodiments of the process 100 that analyze both eyes of a subject, a first set of facial landmarks is assigned to a first iris and assigning 108 a second set of facial landmarks is assigned to a second iris.

Further, the process 100 comprises extracting at 110 raw movement data, from the captured video, of the facial landmark in response to the regimented pattern. Raw movement data can include, but is not limited to, position of the iris in relation to the stimulus, position of the pupil in relation to the stimulus, corrections or adjustments made by the bounded region in response to facial movement, and position of landmark points (i.e., facial landmarks) in relation to the stimulus. Extraction of the raw movement data can be performed in real-time as the video is captured or from stored video at a later time. In this regard, the raw movement data itself can be stored in any suitable storage medium for later processing and analysis.

Further, in embodiments where both eyes are analyzed raw movement data may be extracted from the captured 104 video to correspond to the first set of facial landmarks independently of extracting 110 raw movement data for the second set of facial landmarks.

Moreover, the process 100 comprises creating 112 filtered movement data from the raw movement data based on the facial landmark. Generally, filtered movement data refers to one or more portions of raw movement data (e.g., position of the iris in relation to the stimulus) that are relevant based on circumstances for ocular analysis. The relevant portions of raw movement are analyzed, while the rest of the raw movement data is ignored or removed.

Even further, portions of raw movement data that are relevant may nonetheless be ignored or removed if it is determined that the raw movement data contains erroneous or corrupted data.

For example, aspects of the process 100 may analyze the raw movement data by comparing the facial landmark between distinct frames of the captured video. From the analysis, aspects of the process 100 may determine an existence of a variance between the facial landmark at the distinct frames of the captured video (e.g., the facial landmark, which should be in a fixed position, changes location between the distinct frames). If a variance exists, aspects of the process 100 can identify a select frame (or frames) of raw movement data, from within the distinct frames, as erroneous data if the variance corresponding to the select frame (or frames) of raw movement data exceeds a predetermined threshold. If the variance exceeds the predetermined threshold, aspects of the process 100 can remove the erroneous data from the raw movement data, thus creating filtered movement data.

In various embodiments, the process 100 may further comprise blink detection, which can be accomplished by assigning landmark points to various points of an eye. The process 100 then uses the various points to calculate an eye aspect ratio. If the eye aspects ratio falls below a threshold, the eye is considered to be blinking due in part because the iris is partially covered or disappears entirely.

Still referring to FIG. 1, the process 100 comprises comparing at 114 the filtered movement data to a predetermined movement response that is based on the regimented pattern. In various embodiments, comparing the filtered movement data to a predetermined movement response that is based on the regimented pattern, comprises comparing the filtered movement data against a previously collected version (e.g., a base line) of the filtered movement data, a test population data of collected filtered movement data, or both.

For instance, in a scenario where a sports team is getting ready to start a season, a coach or trainer may analyze each player to collect a base line (i.e., previously collected base line of the filtered movement data). If, during the season a player needs to be analyzed or assessed, the coach or trainer can compare current filtered movement data and the predetermined movement response that is based on the regimented pattern against the previously collected base line of the filtered movement data.

One advantage of using the previously collected base line of the filtered movement data is that each player, while potentially similar in age and/or size, may vary considerably in other physical and mental capacities. For instance, players can have very different reaction times, visual acuity, ocular health, neurological health, side effects due to medication or other external influences from one another. Therefore, having previously collected base lines of each player may yield more accurate results for the analysis, thus improving the field of portable diagnostics.

In further embodiments, each player may have a custom profile that includes a previously collected base line and partial or complete medical records or information that may be pertinent to analysis (e.g., current medications, surgeries, etc.).

Alternatively, if a previously collected base line is not available, the filtered movement data and the predetermined movement response that is based on the regimented pattern can be compared against a test population data of collected filtered movement data.

Continuing from the above scenario, the test population data of collected filtered movement data may comprise individuals of similar physical profiles and activity profiles. For instances, the individuals may be categorized or based on age, weight, height, ethnicity, athletic profile (e.g., sports they play), biological sex, etcetera.

Still referring to FIG. 1, the process 100 comprises generating at 116 a performance score based on the comparison and generating at 118 an output based on the performance score.

Device and the Stimulus

Figure 2:
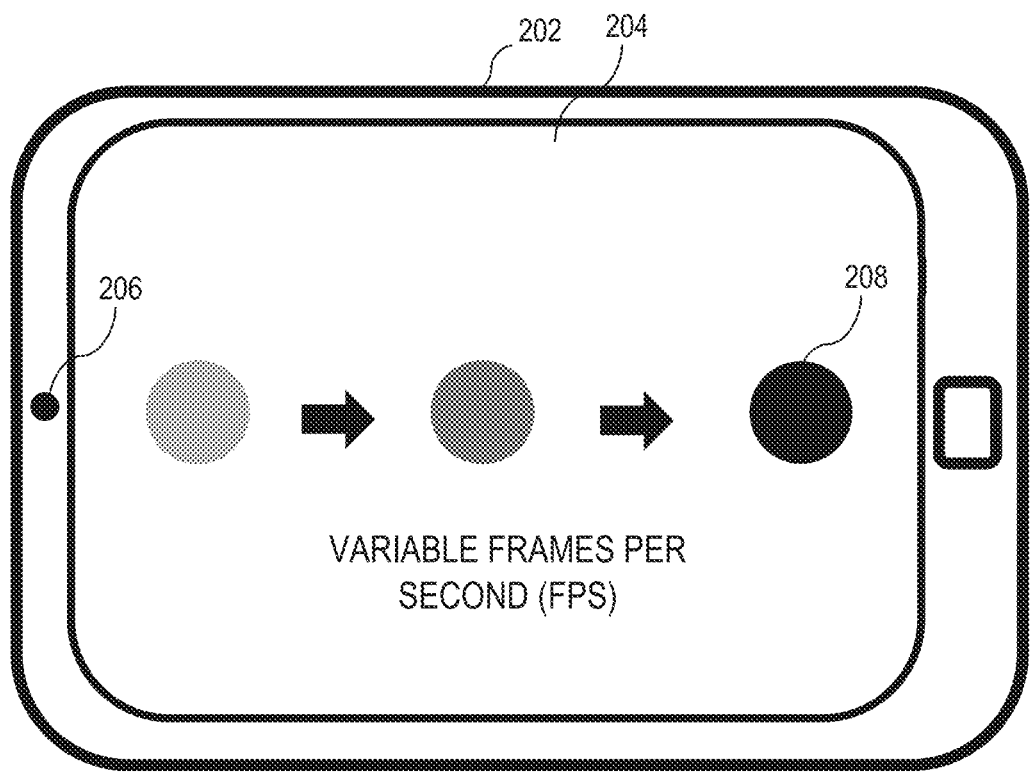
FIG. 2 is an example embodiment of a device displaying a regimented pattern according to various aspects of the present disclosure as described in greater detail herein.

One example implementation of a device is illustrated in FIG. 2. The device 202 has a display 204 and a camera sensor 206, and the stimulus 208 is shown on the display screen 204. With respect of the stimulus 208, any number of movements or patterns of motion may be used as described in greater detail herein. Further, the camera sensor 206 may be on a front facing side of the device 202, a rear facing side of the device 202, or any other suitable side of the device. In various embodiments, there may be more than one camera sensor 206.

With respect to the display 204 and the camera sensor 206, there is no strict requirement for a particular resolution in terms of video definition and video capture. For example, the display 204 may produce images or video equivalent to 480p, 720p, 1080p, 4k, etcetera. Likewise, the camera sensor 206 may capture video or images of similar or different resolution in relation to the display 204.

In FIG. 2, the stimulus 208 is moving from left to right as indicated by the directional arrows. Other regimented patterns include but are not limited to the stimulus 208 having a point that is stationary and unmoving for a predefined period of time, jumping from one location to another after a predetermined period of time, smoothly translating from one location to another over a period of time (e.g., sine function for velocity of linear movement), changing in intensity, moving in a circular pattern (e.g., in a circle at a constant radius and velocity), moving in a spiral pattern (constant angular velocity or constant velocity), moving in a random pattern, or combinations thereof. In various embodiments, the stimulus 208 may be displayed as a customized series of regimented patterns based upon inputs from a user that correspond to test parameters associated with a state of brain function (e.g., test for parameters associated with a brain injury).

Visually, the stimulus 208 may present a solid field of a single color and the point tracking is depicted as a dot that is roughly 5% of a width of the screen. Multiple color combinations can be utilized. For example, a color combination of a dark blue field with a white dot provides easy viewing without excessive eye strain. Higher contrast combinations are preferred due to their effectiveness. However, any combination of colors could be utilized. Further, the point (or stimulus 208) can be "gamified" or animated to be more playful or engaging. For example, a top down view of a car driving on the road or a bee flying over a hive.

Moreover, in some embodiments the stimulus 208 can be displayed at a specified frame rate, which may be measured in frames-per-second (FPS). In other embodiments, the FPS associated with the stimulus may be variable (i.e., within a specified range) or dynamic (e.g., changes in response to lower camera sensor frame rate) based on need.

Further implementations with respect to the stimulus are discussed in further detail herein.

Feature Isolation

Figure 3A:
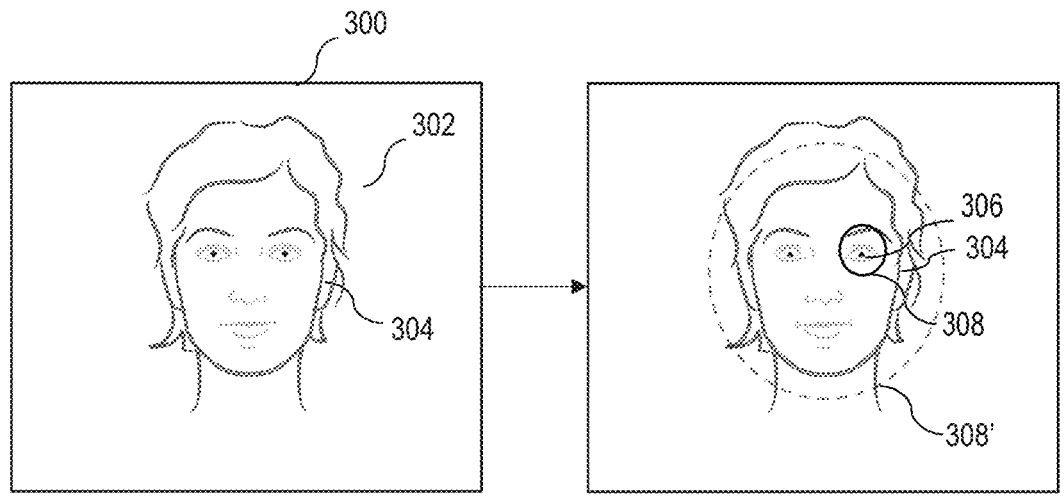
FIG. 3A is an example of isolating an iris as a bounded region according to various aspects of the present disclosure as described in greater detail herein.

FIG. 3A is an example of isolating an iris (see reference number 106 in FIG. 1) as a bounded region. FIG. 3A has capture area 300, which is a viewing area that may be captured or recorded by the camera sensor. Within the capture area 300 is an environment 302, which includes a subject 304 having an iris 306. When the iris 306 has been identified, a bounded region 308 is associated with the iris 306 (e.g., superimposed, overlaid, or surrounds the iris 306). Further, the bounded region 308 can be analyzed to more precisely locate the iris 306.

For example, various analyses to locate the iris 306 (or other features) within the bounded region 308 can be performed via image recognition techniques including, but not limited to pattern recognition, machine learning, principal components analysis, self-organizing maps, hidden Markov models, or combinations thereof.

Further, one or more characteristics of the landmarks within the bounded region 308 (or the capture area 300 as a whole) can be emphasized via digitally enhancement including, but not limited to, contrast adjustment, color correction, softening, smoothing, sharpening, edge detection, or combinations thereof.

The bounded region 308 can be strictly constrained to the iris 306 or can include a larger portion the subject 304 such as the subject's face (see reference number 308') as shown in FIG. 3A. Further, a user can manually adjust the distance between the mobile device and the subjects face to ensure nominal positioning. the user may use a touch screen or other interface to manually isolate the iris 306.

In another example of isolating the iris 306, the process (100, FIG. 1) maps the bounded region 308 and subsequently tracks the iris 306 in a smaller bounded region, which can be scaled to appropriate size. In this regard, one or both irises may be isolated.

Figure 3B:
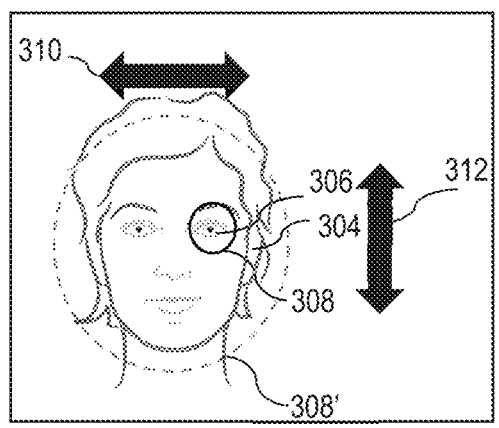
FIG. 3B is an example the bounded region of FIG. 3A adjusting to movement according to various aspects of the present disclosure as described in greater detail herein.

Now referring to FIG. 3B, in various embodiments, the bounded region 308 can be modified to adapt or correct for movements of the iris (i.e., the bounded region 308 dynamically moves to keep the iris 306 within the bounded region 308) as shown by horizontal arrows 310 and vertical arrows 312. The capability for the bounded region 308 to adapt to movements of the iris 306 (e.g., translation or rotation of head or the iris 306) allows both the subject 304 and the camera sensor to be unconstrained (i.e., not fixed in relationship to one another). In various embodiments, wherein the bounded region 308' isolates the face of the subject 304, the bounded region 308' can be modified to adapt or correct for movements of the face of the subject 304, thus yielding an improvement over existing solutions that required the camera sensor to be fixed in relation to the subject.

As mentioned above, blink detection can be accomplished by landmark assigning points to various points of an eye. The various points are used to calculate an eye aspect ratio, and if the eye aspects ratio falls below a threshold, the eye is considered to be blinking, because (at least in part) the iris 306 is partially covered or disappears entirely.

Figure 4:
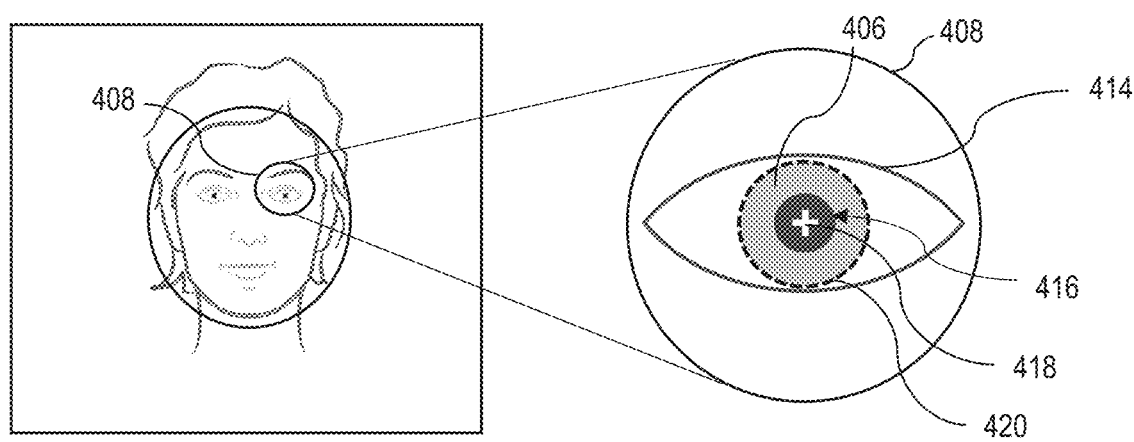
FIG. 4 is a further example of isolating an iris according to various aspects of the present disclosure as described in greater detail herein.

FIG. 4 illustrates a further example of isolating an iris. The example of FIG. 4 is analogous to FIGS. 3A and 3B, except that the reference numbers in FIG. 4 are 100 higher. Further, all references to FIG. 4 can incorporate the various processes, definitions, and embodiments disclosed in FIGS. 1-3 can be combined in any combination of components described with reference thereto. In this regard, not every disclosed component need be incorporated.

In the example of FIG. 4, the bounded region 408 includes an eye 414, which comprises an iris 406 and a pupil 416. In various embodiments, one facial landmark 418 may constitute the assigned facial landmark 418. In FIG. 4, the facial landmark 418 is a center of the iris (or alternatively the pupil), which is denoted as a white cross. One advantage of using the center of the iris is that an outer diameter of the iris is a constant diameter and higher contrast (in the visible spectrum) than the pupil. Conversely, if infrared technology is used, then isolating the pupil may suitable as well.

In practice, however, assigning more than one facial landmark 418 (e.g., a set of landmarks 420 as shown in FIG. 4 around the center of the iris) may allow for a higher confidence level when tracking the eye 414 by having more points of differentiation. While FIG. 4 only shows one eye 414 and corresponding landmark point 418, in practice both eyes may be utilized.

The following examples represent rule-based sets that are targeted for error detection and removal as described herein.

Example of Creating Filtered Movement Data—Characteristics

Figure 5A:
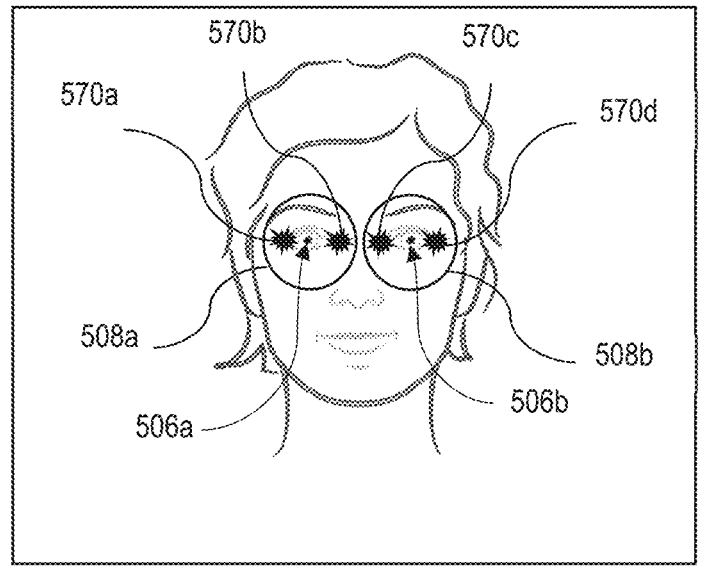
FIG. 5A illustrates a first example of checking for errors in data according to various aspects of the present disclosure as described in greater detail herein.
Figure 5B:
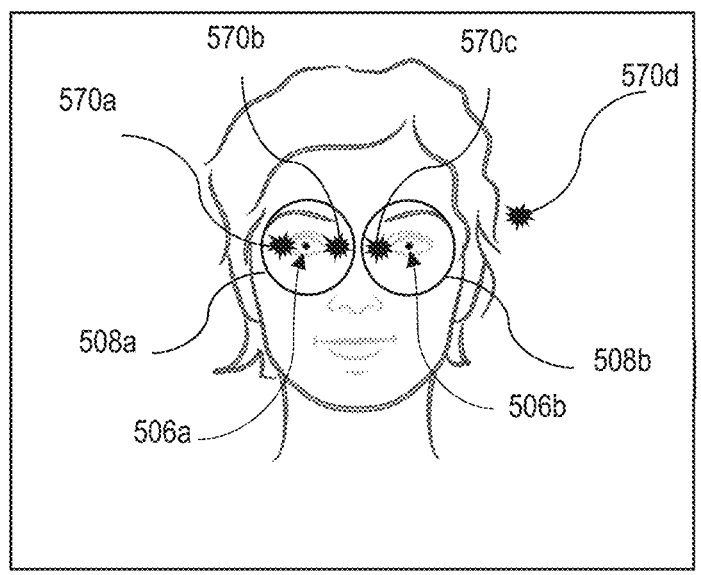
FIG. 5B further illustrates the first example of checking for errors in data according to various aspects of the present disclosure as described in greater detail herein.

FIG. 5A illustrates an example for creating filtered movement data as described above. The examples of FIGS. 5A and 5B are analogous to FIGS. 3A and 3B, except that the reference numbers in FIGS. 5A and 5B are 200 higher. Further, all references to FIGS. 5A and 5B can incorporate the various processes, definitions, and embodiments disclosed in FIGS. 1-4 can be combined in any combination of components described with reference thereto. In this regard, not every disclosed component need be incorporated.

In FIG. 5A one embodiment for determining the existence of a variance between distinct frames of captured video is to identify whether a facial landmark is within a bounded region at distinct frames of captured video as described below. Moreover, the embodiment comprises removing the select frame of captured video when the facial landmark is outside the bounded region.

For example, in FIG. 5A, a first iris 506*a* has a corresponding first bounded region 508*a* and a second iris 506*b* has a corresponding second bounded region 508*b*. For this example, a first reference point 570*a* and a second reference point 570*b* are within the first bounded region 508*a*, and a third reference point 570*c* and a fourth reference point 570*d* are within the second bounded region 508*a*. The reference points 570*a-d* may be facial landmarks (i.e., assigned facial landmarks) or artificial markers (e.g., reference markers) that are placed during video capture. FIG. 5A conceptually can be thought of as a single or distinct frame of captured video.

FIG. 5B illustrates a single image of the same video used to generate the frame of FIG. 5A, except that the fourth reference point 570*d* is found outside of the second bounded region 508*b* (i.e., has changed in position). This may be cause by the subject moving quickly, the camera being moved, a malfunction in the camera, or combinations thereof. Therefore, the FIG. 5B is removed as erroneous data. Through this detection and removal of erroneous data, the camera sensor is not required to be fixed in relation to the subject.

From a technical standpoint, while it is possible to find variances and remove frames of captured video that contain the variances using only two distinct frames of captured video, in practice using multiple distinct frames of captured video is preferred.

Example of Creating Filtered Movement Data—Fixed Distance

Figure 6A:
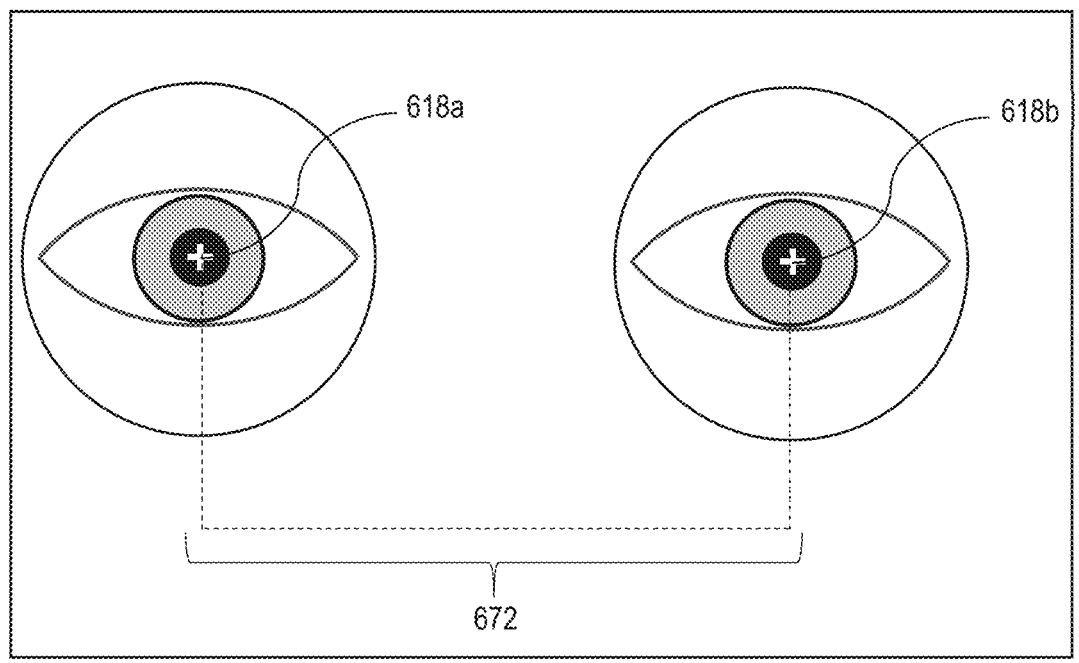
FIG. 6A illustrates a second example of checking for errors in data according to various aspects of the present disclosure as described in greater detail herein.
Figure 6B:
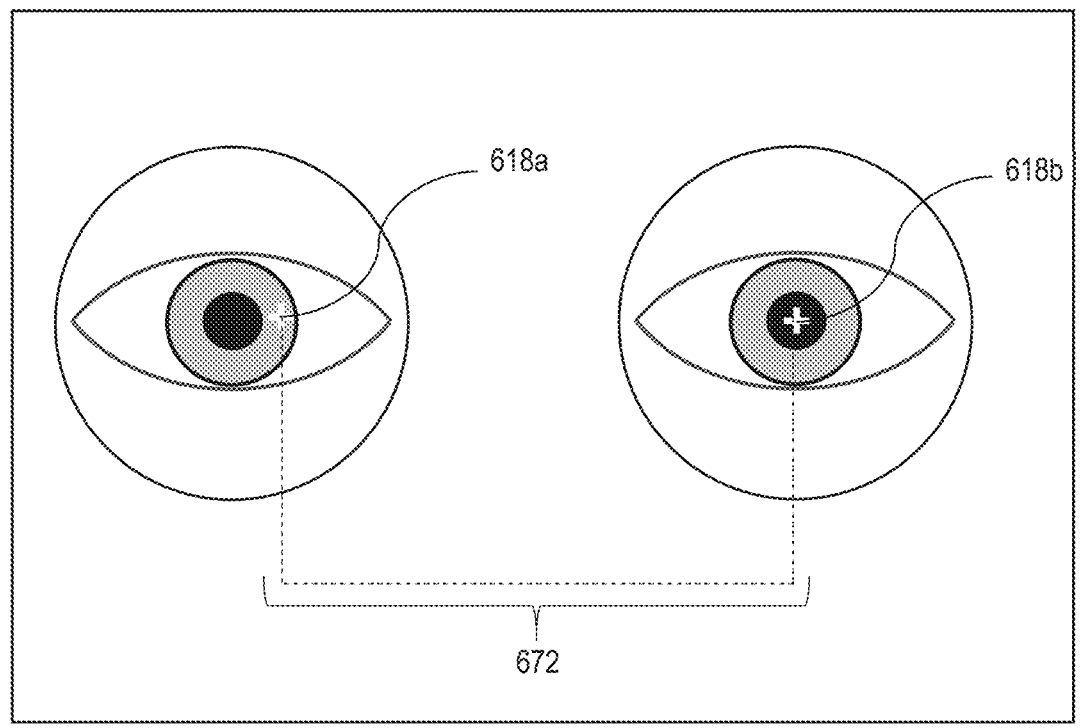
FIG. 6B further illustrates the second example of checking for errors in data according to various aspects of the present disclosure as described in greater detail herein

FIG. 6A illustrates an example for creating filtered movement data as described above. The examples of FIGS. 6A and 6B are analogous to FIGS. 3A and 3B, except that the reference numbers in FIGS. 6A and 6B are 300 higher. Further, all references to FIGS. 6A and 6B can incorporate the various processes, definitions, and embodiments disclosed in FIGS. 1-5 can be combined in any combination of components described with reference thereto. In this regard, not every disclosed component need be incorporated.

Another embodiment for determining the existence of a variance between distinct frames of captured video is calculating a distance between facial landmarks and compare the distance between distinct frames as described below.

A distance is calculated between a first targeted facial landmark and a second targeted facial landmark. In some embodiments, the targeted facial landmarks are selected from within the bounded region. Further, various embodiments comprise determining if the calculated distance between the first targeted facial landmark and the second targeted facial landmark remains consistent at distinct frames of the captured video. Moreover, the embodiment comprises identifying a select frame of raw movement data as erroneous data comprises determining whether a change in the calculated distance between the first targeted facial landmark and the second targeted facial landmark exceeds a predetermined threshold in the select frame of raw movement data and removing the select frame of captured video if the variance exceeds the predetermined threshold.

For example, in FIG. 6A, a distance 672 between a first targeted facial landmark 618a in a first bounded region 608a and a second targeted facial landmark 618b in a second bounded region 608b is calculated. In this example, a variance is a change in the calculated distance 672. If the change in the calculated distance 672 (i.e., the variance) between the first targeted facial landmark 618a and the second targeted facial landmark 618b exceeds a predetermined threshold, as is the case in FIG. 6B, the select frame of captured video is removed.

Example of Creating Filtered Movement Data—Spatial Relationships

Figure 7A:
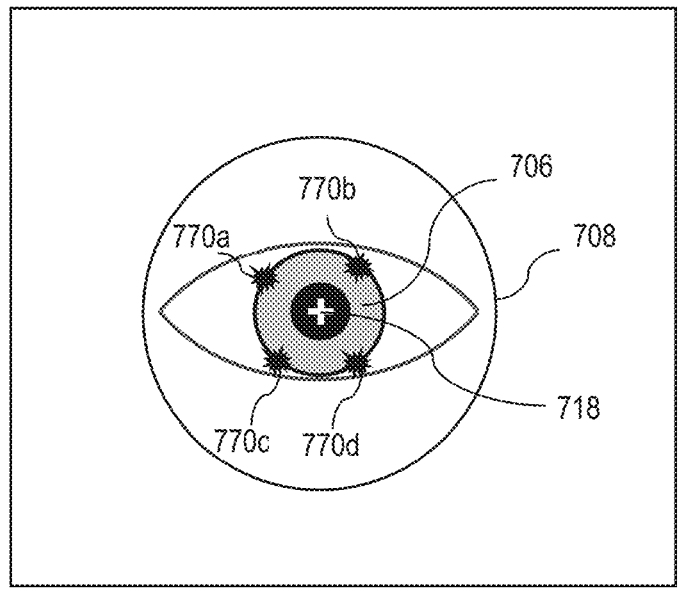
FIG. 7A illustrates a third example of checking for errors in data according to various aspects of the present disclosure as described in greater detail herein.
Figure 7B:
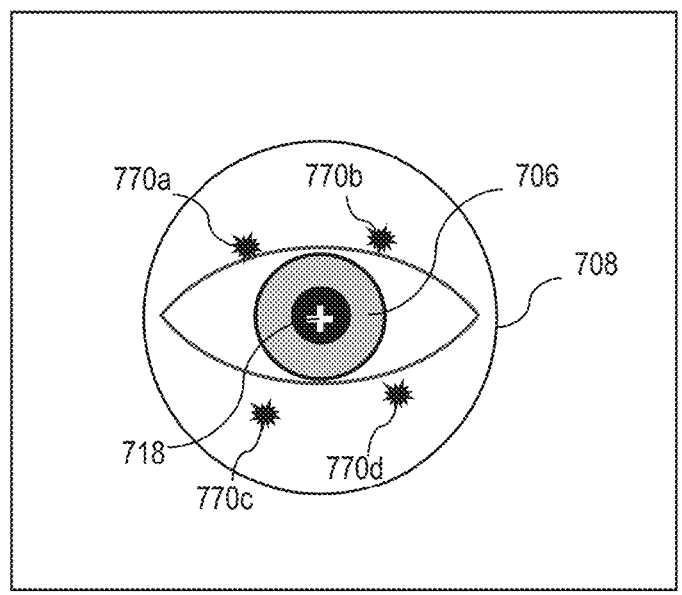
FIG. 7B further illustrates the third example of checking for errors in data according to various aspects of the present disclosure as described in greater detail herein.

FIG. 7A illustrates an example for creating filtered movement data as described above. The examples of FIGS. 7A and 7B are analogous to FIGS. 3A and 3B, except that the reference numbers in FIGS. 7A and 7B are 400 higher. Further, all references to FIGS. 7A and 7B can incorporate the various processes, definitions, and embodiments disclosed in FIGS. 1-6 can be combined in any combination of components described with reference thereto. In this regard, not every disclosed component need be incorporated.

One embodiment for determining the existence of a variance between distinct frames of captured video is by comparing characteristics of sets of facial landmarks at distinct frames of the captured video as described below.

The embodiment comprises selecting a set of facial landmarks wherein the set of facial landmarks includes the facial landmark corresponding to the iris. The embodiment further comprises comparing characteristics of the set of facial landmarks at a select frame of the distinct frames of the captured video. Moreover, the embodiment comprises determining whether the characteristics of the set of facial landmarks exceed a predetermined threshold in the select frame of raw movement data and removing the select frame of raw movement data wherein the characteristics of the set of facial landmarks exceed the predetermined threshold.

FIG. 7A illustrated a single frame of captured video. In FIG. 7A, a facial landmark 718 is on the center of an iris 706 within a bounded region 708. For this example, a first facial landmark point 770a, a second facial landmark point 770b, a third facial landmark point 770c, and a fourth facial landmark point 770d are also within the bounded region 708. The facial landmarks 718, 770a-d may be reference points, or artificial markers that are placed during video capture.

In this example, the facial landmark points 770a-d comprise a set of facial landmark points that correspond the facial landmark 718 in a fixed relationship (i.e., fixed in distance in relation to the facial landmark 718). Thus, the "characteristic" of a fixed relationship between the set of facial landmarks in relation to the facial landmark 718 (e.g., a radius around the center of the iris 706) is used to determine whether a variance is present. For this example, if the variance does exceed the predetermined threshold, the select frame of raw movement data would be removed as erroneous data.

Furthermore, if any landmarks within the set of facial landmarks 770a-d have a variance above a set threshold when compared to itself in subsequent frames, the subsequent frame or frames of raw movement data would be removed as erroneous data.

FIG. 7B illustrates an example where the set of facial landmark points 770a-d in relation to the facial landmark 718 has changed. Further, landmarks within the set of facial landmarks 770a-d when compared to themselves has changed as well. If either change exceeds the respective threshold, then the select frame(s) of raw movement data may be removed.

From a technical standpoint, while it is possible to find variances and remove frames of captured video that contain the variances using only two distinct frames of captured video, in practice using multiple distinct frames of captured video is preferred.

Adaptive/Composite Test Generation

Figure 8:
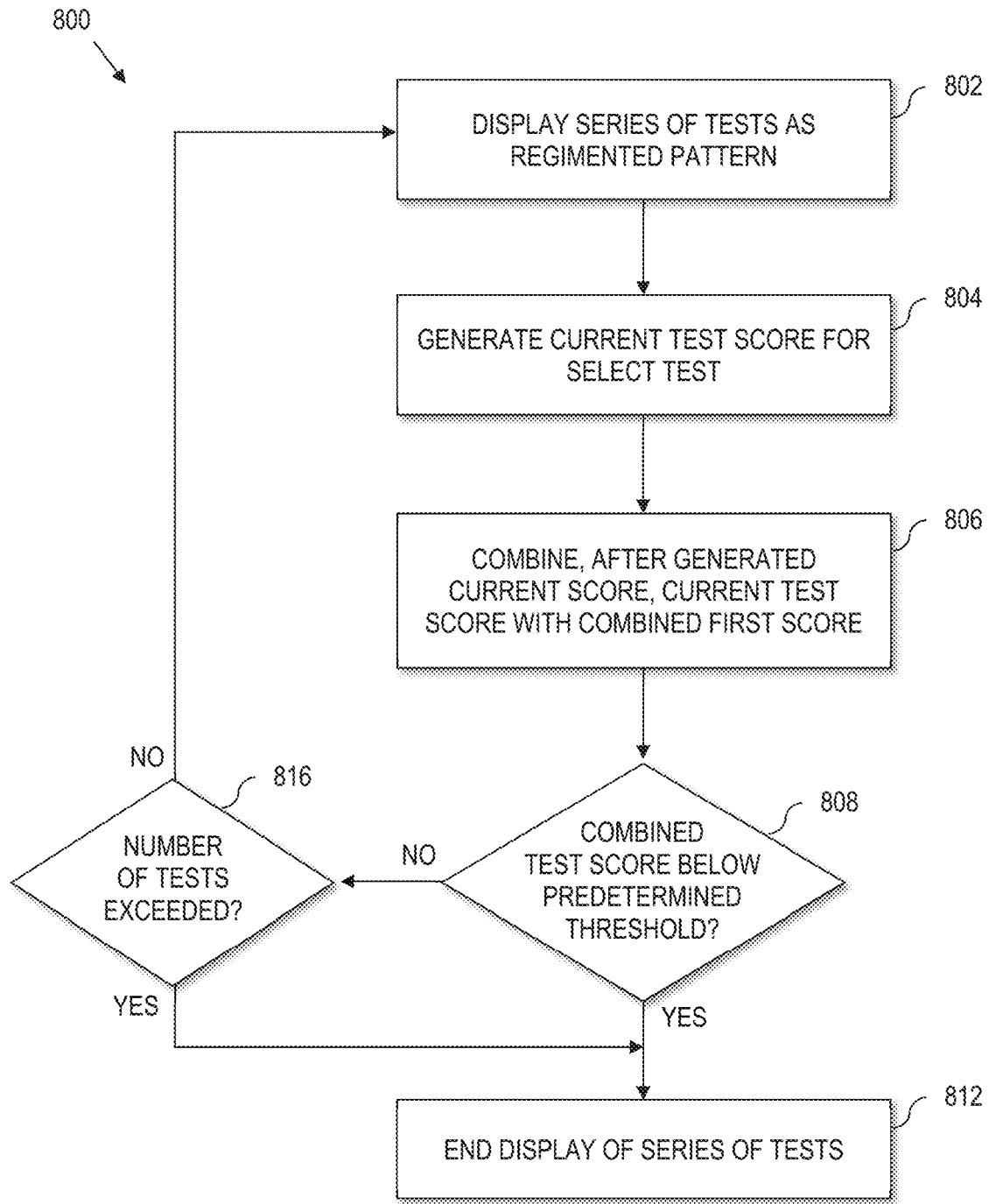
FIG. 8 illustrates a flow chart for adaptive test scoring according to various aspects of the present disclosure as described in greater detail herein.

FIG. 8 illustrates a flow chart 800 applicable to various embodiments of the process 100 (hereinafter "the process" for this example) that generate 116 test scores. Further, all references to FIG. 8 can incorporate the various processes, definitions, and embodiments disclosed in FIGS. 1-7 can be combined in any combination of components described with reference thereto. In this regard, not every disclosed component need be incorporated.

The process 800 comprises displaying at 802 a series of tests as a regimented pattern. Further, the process comprises generating 804 a current test score for the selected test after it is displayed 802. Yet further the process 800 comprises combining, at 806, after the current test score is generated, the current test score with a combined test score.

As shown at 808, when the current test score is combined with the combined test score, a change in the combined test score is calculated, and if the change in the combined test score is below a predetermined threshold, then the process determined that subsequent test scores will probably not affect the outcome of the series of tests, so the process 800 ends and does not display subsequent test scores.

If, however, the change in the combined test score is not below a predetermined threshold, then the process comprises determining whether a number of tests taken exceeds a predetermined threshold at 816. If the number of tests taken exceeds the predetermined threshold, then the process ends at 812. However, if the current number of displayed tests is below the predetermined threshold, then the process 800 loops back to 802 to display another test. Thus, the process continues until the number of tests taken exceeds the threshold, or the change in the combined 806 test score is below predetermined threshold.

Example of Adaptive/Composite Test Generation

FIG. 9 illustrates an example composite ocular test 900 that can be performed by the process 100. The table contains a regimented pattern (i.e., stimulus) motion 902 and an associated duration 904 for each regimented pattern motion 902. Each row of FIG. 9 under the regimented pattern motion 902 can be considered to be a single ocular test. In the example test 900, a total composite test time 906 for this example test 900 is forty-nine-and-a-half (49.5) seconds. The regimented pattern motions 902 and associated durations 904 are by way of example and are not limiting.

In a practical example, a doctor suspects that a patient with a head injury might have a concussion. The doctor has an embodiment of the devices described herein, which has the requisite hardware and software to perform the processes described herein. Given that that doctor believes that the patient may have a concussion, the doctor selects a series of tests that test and analyze for concussions.

In this example, a change in the combined score of two is used as the predetermined threshold to determine whether to continue with the tests, and a maximum number of tests is ten. The device displays a first test and generates a score of eighty. Since only one test has been displayed, there is no second score to combine. Therefore, the process continues to display a second test (e.g., either the same test as the first test or a different test in the case of a composite test as seen in FIG. 9). A second test score of 70/100 is generated from the second test. In this example, the scores are combined by averaging the tests scores. However, other methods of combining the scores may be used (e.g., summing the scores, concatenating the scores, weighting the scores, etc.).

When the second score is combined with the combined score, the combined score is no longer 80 but is now 75. The change in the combined score is five, which is still above the predetermined threshold, so the device displays a third test, which includes a score of 74. When averaged with the combined score, the new combined score is 74.67, which includes a change in the combined score of 0.67, which being below the predetermined threshold of two the device stops displaying tests.

However, if the change in the combined scores are always above two, then after ten tests being displayed, the device would stop displaying tests, because the maximum number of tests to be displayed is ten.

Optionally, after ten tests are displayed, the process could instead provide an alternate or augmented series of results in which the doctor is prompted to retake one or more tests, or a score can be presented with an indicator of lower confidence.

By allowing users to set thresholds and select tests that are specific to a particular disruption in the normal function of the brain, higher confidence levels can be achieved when compared to previous solutions.

Data Optimization

In addition to creating filtered movement data by removing bad frames or bad data, data can be optimized by analyzing specific portions of data, or windows of interest within the data that are pertinent to the analysis based on the circumstances. In such embodiments, the process (100, FIG. 1) comprises overlaying the raw movement data of the facial landmark in response to the regimented pattern onto a corresponding point in time during the captured video. The process further comprises selecting a window of interest based on the corresponding point in time. Moreover, the process comprises comparing the raw movement data of the facial landmark in response to the regimented pattern within the selected window of interest. The window of interest can also be selected based off a change in the regimented pattern. For the purposes of this disclosure, overlaying means selecting a portion of data for each the filtered movement data and the predetermined movement response and matching them with a corresponding point in time.

For example, the window of interest may be defined as 25% to 50% of the stimulus motion where the full stimulus motion is defined as 0-100%. Alternatively, window of interest may be 100-360 milliseconds (ms) after a substantial change in stimulus position.

Figure 10A:
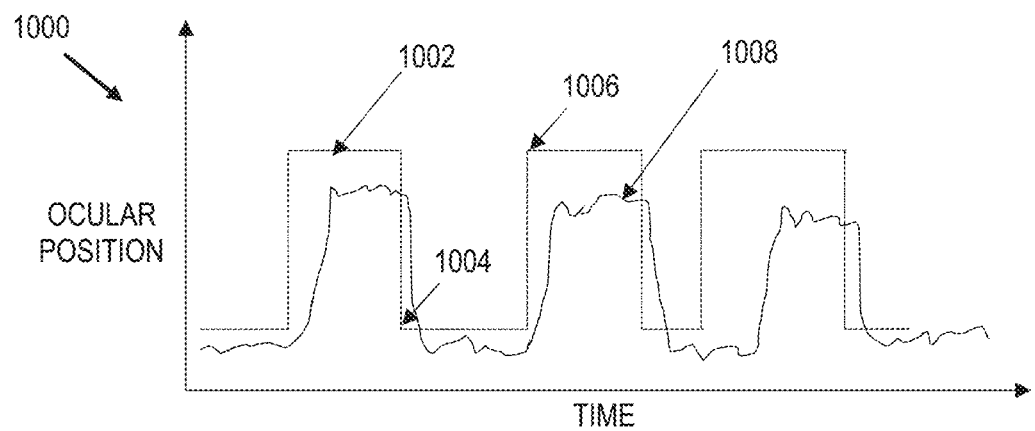
FIG. 10A illustrates a saccades graph showing illustrating a relationship between a regimented pattern and eye movement according to various aspects of the present disclosure as described in greater detail herein.

For example, FIG. 10A illustrates a graph 1000 of tracked eye movements in response to a stimulus motion. The graph is structured as ocular position over time. The stimulus motion 1002 is moving in a pattern that tests saccadic performances (i.e., instantly moving the point from one position to another). Generally, saccades refer to a rapid movement of the eye between fixation points. Each fall 1004 and rise 1006 indicate a change in position of the stimulus motion 1002. Accordingly, eye movements 1008 tend to correspond to the stimulus motion 1002.

In certain implementations of the process, the graph 1000 may be used in its entirety to generate 116 performance scores, excluding any bad frames or bad data. However, other aspects of the process 100 utilize windows of interest to focus on specific (e.g., relevant) data.

Figure 10B:
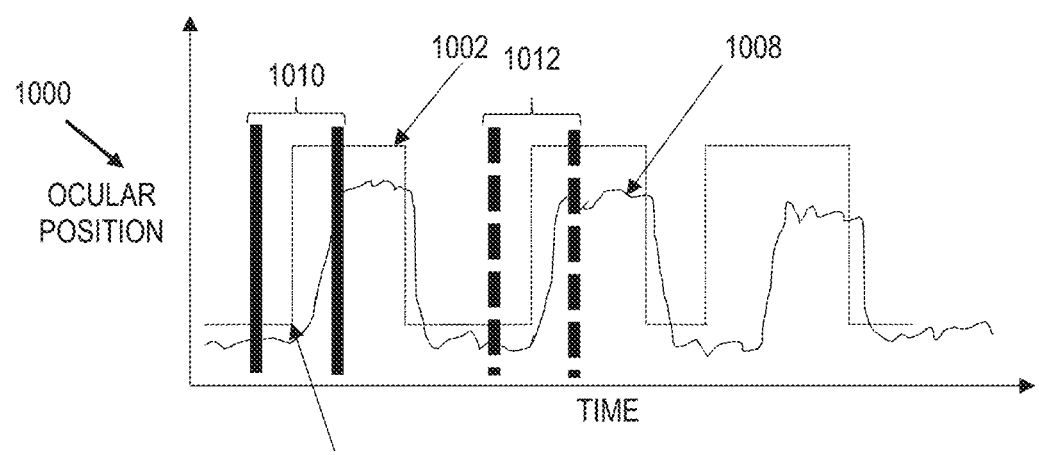
FIG. 10B is a graph further illustrating the relationship between the regimented pattern and eye movement of FIG. 10A according to various aspects of the present disclosure as described in greater detail herein.

Turning to FIG. 10B, given that the stimulus motion 1002 is based on saccadic motion, the primary focus is on portions of the graph 1000 data where the stimulus motion 1002 changes (e.g., the fall 1004). Accordingly, a window of interest 1010 is that corresponds with the stimulus motion 1002 changes. In various embodiments, more than one window of interest 1010 may be utilized (see second window of interest 1012 in dashed lines). As shown, the window of interest is centered around the change in the position of the point used as a stimulus (thus, the window starts before the change in position). However, the window may start at the change in position or after the change in position.

Figure 10C:
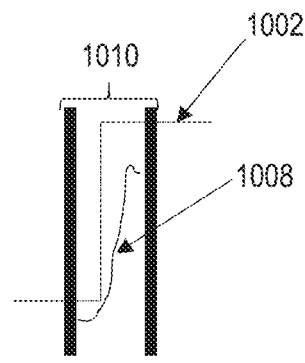
FIG. 10C illustrates a window of interest within the relationship between the regimented pattern and eye movement of FIG. 10B according to various aspects of the present disclosure as described in greater detail herein.

In some embodiments the movement data outside the window of interest is not stored. In other embodiments, the camera sensor is not activated except during the window of interest (i.e., no data is collected outside the window of interest). FIG. 10C illustrates the window of interest 1010 with all other data removed.

Figure 10D:
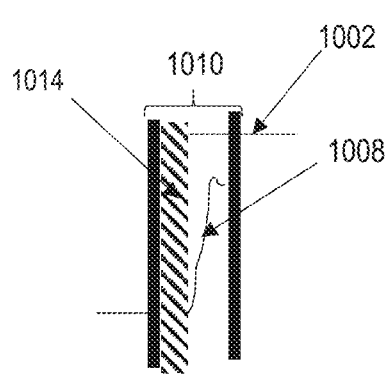
FIG. 10D further illustrates the window of interest within the relationship between the regimented pattern and eye movement of FIG. 10C according to various aspects of the present disclosure as described in greater detail herein.

Turning to FIG. 10D, the process in various embodiments may also remove erroneous data 1014 from the window of interest 1010 using the processes and techniques described herein, thus further narrowing the amount of data that the process needs to analyze. When properly implemented, windows of interest 1010 can speed up processing time and achieve results with a higher degree of confidence by removing less relevant, erroneous, or bad data.

Figure 11A:
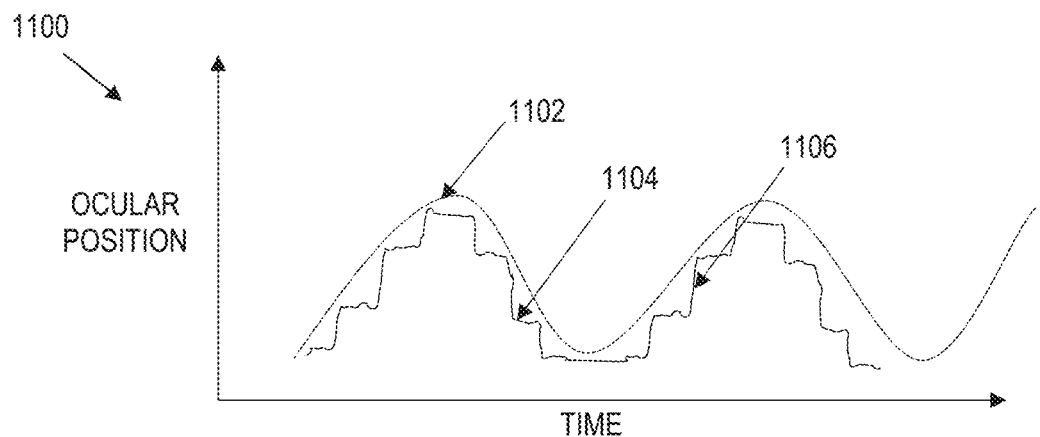
FIG. 11A is a smooth pursuit graph showing illustrating a relationship between a regimented pattern and eye movement according to various aspects of the present disclosure as described in greater detail herein.

Now referring to FIG. 11A, which illustrates a graph 1100 of tracked eye movements in response to a stimulus motion (similar to the graph of 1000), except that the stimulus 1102 in 1100 is based on sinusoidal motion. Sinusoidal stimuli move from one side of the screen to the other in a set frequency (or frequencies). Sinusoidal velocity profiles are useful for gauging "smooth pursuit" of an eye (hereinafter "smooth pursuit test").

Figure 11B:
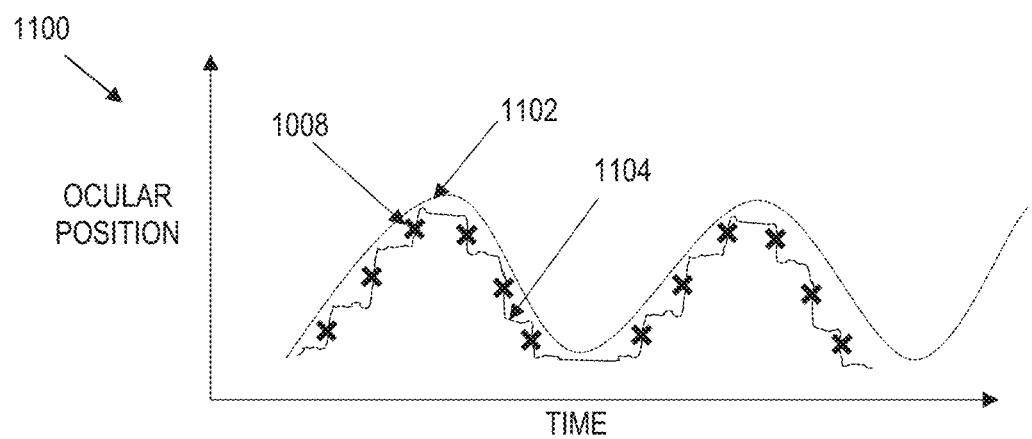
FIG. 11B is a graph further illustrating the relationship between the regimented pattern and eye movement of FIG. 11A according to various aspects of the present disclosure as described in greater detail herein.

In FIG. 11A, the graph 1100 has a stimulus motion 1102 line and a tracked eye movement 1104 line. Typically, a human eye cannot perfectly stay in sync with the stimulus motion 1102, thus resulting in the human eye speeding up or making jumps (or "micro-saccades") 1106 to keep up with the stimulus motion 1102. These micro-saccades 1106 present as vertical lines (similar to saccadic motion) on the graph 1100. Generally, the micro-saccades 1106 data are not pertinent data for the smooth pursuit test. Thus, the micro-saccades 1106 are removed as shown in FIG. 11B as designated by the "X" marks 1108 (the stimulus motion 1102 and tracked eye movement 1104 line are shown for clarity).

Figure 11C:
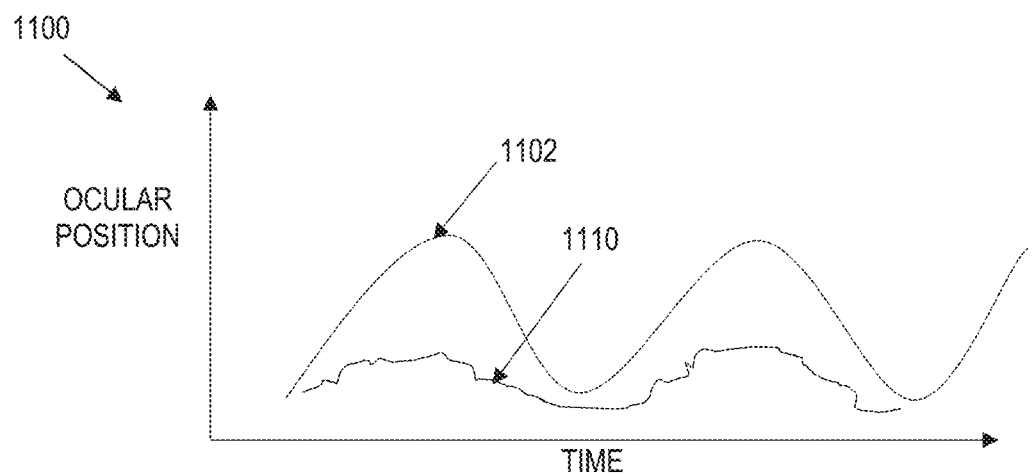
FIG. 11C is a graph yet further illustrating the relationship between the regimented pattern and eye movement of FIG. 11B according to various aspects of the present disclosure as described in greater detail herein.

In FIG. 11C, with the micro-saccades 1106 removed, the process 100 transforms the tracked eye movement 1104 into a smoothed equivalent tracked eye movement 1110 line focused exclusively on the smooth pursuit portion of the data. Essentially, FIG. 11C has removed all saccadic eye motion data.

Further, given that in multiple embodiments, there is no expectation to see rapid head motion, the position of the head need not be analyzed in each frame, and the facial landmarks can be found using the "seeds" previously generated as a starting point. Similarly, assuming sufficient head stability, the facial landmarks need not be calculated every frame and the pupil position can be analyzed using the "seeds" previously generated in a frame or two before the current frame.

Application

Multiple aspects of the present disclosure discussed thus far relate to data gathering, data filtering, and data optimization. Portions of the disclosure hereinafter are directed toward application or uses for the various data (e.g., filtered movement data) with respect to ocular analysis.

For example, implementations the process 100 can extract specified data values and compare those values against an associated disruption in the normal function of the brain. In such implementations, the process 100 comprises extracting data values from filtered movement data and the predetermined movement response based on the regimented pattern. The process 100 further comprises comparing the extracted data values against known data values associated with a disruption in the normal function of the brain. Moreover, the process 100 comprises generating a performance score based upon the compared extracted data values with the known data values associated with a disruption in the normal function of the brain.

The results of the implementations of the present disclosure as provided herein effectively transform a device (e.g., a mobile device) into a device that can aid in a TBI diagnosis with little to no change in the device hardware. Rather than simply collect and organize data, which may be found in other prior solutions, the present disclosure produces output that solicits responses and information from a user. Those responses and information are then used to generate outputs that are specific and tangible to the user (e.g., an indication or likelihood of a disruption in normal brain function). Thus, an existing device (e.g., a cell phone, a computer, etc.) can be transformed into an ocular analyzer using the processes described herein.

Types of Tests

FIG. 12 illustrates a table 1200 that correlates types of tests 1202, including various metrics (or measurements) 1204 that correspond to the types of tests 1202. The types of tests 1202 and metric 1204 are matched with probability values 1206 indicative of a disruption in the normal function of the brain.

The types of tests 1202 include, saccades, self-paced saccades, smooth pursuit, gaze, nystagmus, vergence, pupil response, accommodation, sport concussion assessment tool (SCAT) 3, anti-saccades optokinetic (OPK), memory saccades, hemistim, random saccades, and other cognitive or neurological assessments.

Metrics 1204 that correspond to the types of tests 1202 include, but are not limited to time (e.g., seconds (sec), milliseconds (ms), etc.), percentage (%), degrees (e.g., deg), degrees over time (e.g., deg/sec), numerical count (e.g., 1), length (e.g., inches (in), centimeters (cm), etc.), and presence (yes or no, Y/N).

Saccades Test

For saccades testing, the stimulus moves from one stationary location to another on opposite or nearly opposite sides of the screen. Once the movement has occurred, the stimulus remains in the new location for a random period of time (e.g., between 1 and 2 seconds). Then, the stimulus moves again. The numbers and duration may vary.

One metric associated with saccades testing is latency. Latency is the period from when the stimulus moves to when the eye moves to follow. A normal latency can be between 150 and 250 ms. The accuracy of this metric is a function of the frame rate (error (ms)=1000/sample rate).

Another metric associated with saccades testing is accuracy. Accuracy looks to how closely the pupil is looking at the correct stimulus location (also referred to as "undershoot" and overshoot"). A normal error is below 10% of the distance traveled. Additionally, small overshoots are more typical for small displacements whereas small undershoots are more typical of large displacements. While exact position is difficult to determine, a magnitude of travel can be tracked and thereby the accuracy can be inferred.

Pupil velocity uses positional data can be converted to temporal data by way of equation $V_p=\Delta X_p/\Delta t=\Delta X_p*F_r$ (where $V_p$ is pupil velocity, $\Delta X_p$ is change in pupil position, $\Delta t$ is time between frames, and $F_r$ is frame rate. In this application, assuming +/− five (5) degrees (deg) pupil rotation, any velocity below 60 deg/sec would not be considered a saccade.

Self-Paced Saccades Test

The self-paced saccades test, which is different than saccades in that the stimulus does not move but rather the subject is asked to shift their focus back and forth between two fixed points as fast as they can. Nominal position for the stimulus is to generate approximately ±15° of horizontal motion from centerline. Traditionally this is done with two fingers spaced 6"-8" apart and 11"-15" from the subject's head.

The self-paced saccades test counts a number of refixations that the subject can accomplish in a given time frame (e.g., 30 seconds), which is compared against a baseline (e.g., a previously collected base line, or a population base line). Further, a mean time between saccades is divided into a non-saccadic duration needed for stimulus accommodation and a duration between primary saccade and a corrective saccade.

Smooth Pursuit Test

For the smooth pursuit test, the stimulus moves from one side of the screen to the other in a set frequency (or frequencies) with a sinusoidal velocity profile at a constant velocity.

One metric associated with the smooth pursuit test is gain, which measure of how well the eye can track the position of the stimulus without the need for saccadic intervention or catch-up saccades. Gain can be measure by non-saccadic velocity, which is a measure of velocity of pupil excluding any catch up saccadic motion divided by the velocity of the pupil if it were perfectly tracking the stimulus (also referring to as velocity of the eye divided by velocity of the stimulus). An ideal gain value by this method is one.

Another metric associated with the smooth pursuit test is 2-D non-saccadic velocity, which is a measure that has an added component of a direction vector of the motion and therefore the velocity is interpreted both in the direction of stimulus motion and normal to the direction of stimulus motion. One example equation is $Gain=V_{eye}*V_{stimuius}/V_{stimulus}$, or $Gain\perp=V_{eye}+V\perp_{stimulus}$. A perfect score would be G=I and G⊥=0. As results deviate further from normal G will decrease and, if the stimulus is not moving in a straight line, G⊥ will increase.

For smooth pursuit, accuracy is measured by analyzed for pupil position versus stimulus position then the error or distance between actual pupil position and stimulus position is recorded. Due to calibration challenges (discussed below), true accuracy is challenging to calculate. However, accuracy based on the calibration data can be determined. The root mean square (RMS) of the video is then calculated, which can be done either for a portion of the video which will generate a localized or rolling RMS score or for the entire length of the video giving a total RMS value. An example equation is $E_{rms} = \sqrt{1/n((X_1-X_{s1})^2+(X_2-X_{s2})^2+ \ldots +(X_n-X_{sn})^2)}$.

Gaze Test

For the gaze test, the stimulus is positioned at a single point on the screen and does not move. An alternate embodiment is to have the subject look at an extreme of their perception and maintain gaze on a target at the extreme.

One metric is gaze stability, which is measured by the RMS error on position deviation. In other words, is the pupil position actively moving or is it securely fixed in a single location. As a subject becomes more susceptible to distraction, or is effected by particular neurologic conditions such as mild traumatic brain injury (mTBI), the RMS value will increase. Accuracy is calculated analogously to smooth pursuit.

Nystagmus Test

The nystagmus test looks for repetitive, uncontrolled movements of the eye. The stimulus can be the same as the gaze test, the smooth pursuit test, or both. Metrics for the nystagmus test include nystagmus (i.e., rapid, uncontrolled eye movement) presence, nystagmus frequency (i.e., how often does a nystagmus event occur in a set period of time), and a mean amplitude (how much eye rotation movement can be detected in an average nystagmus event).

Vergence Test

Vergence (or convergence insufficiency) testing is directed to establishing various focal distances. Traditionally, a ruler is used as the stimulus that progressively moves from approximately two feet away towards the nose. Once the subject can no longer maintain focus, they will alert the test administrator who will measure the distance to determine how close to the nose an object can get while the subject is still able to maintain focus on the object. One issue with the traditional method is that results can be subjective as it relies on the subject to be accurate and quick in their declaration of when the object loses focus.

An improved method for measuring focal length, as disclosed herein uses the camera sensor in-line with the stimulus. After ensuring that the camera is roughly in line with the path of the stimulus, the focal point of the camera can be utilized to measure distance. By using an autofocus feature and focusing on the face and then on the stimulus, the distance between the two can be determined.

Another test for vergence utilized fiducial measuring. Traditionally, a fiducial such as a credit card is used to measure focal length since the fiducial has a known size it can be positioned at the "zero position" and at the point where focus is lost. By comparing the size of the fiducial, the distance between the two can be determined.

In an improved version, the camera is held to the side of the subject and use a known value (such as head height) or a fiducial as a calibration measure to then measure the distance between the subject and the stimulus. Alternatively, stereoscopic imaging can be used.

Alternatively, parallax mechanics can be leveraged by shifting the camera to the side (even slightly) the perceived motion of the stimulus versus the perceived motion of the face can be used to calculate relative distance.

One variant of the vergence test is vergence accommodation. In vergence accommodation, the pupil constriction is monitored in response to the stimulus. The pupil will continue to constrict as the stimulus gets closer to the subject, until focus is lost. At which point further constriction will not occur. Therefore, by monitoring pupil dilation there is no need to rely on the verbal response of the subject.

Pupil Response Test

The pupil response test uses the camera flash to manipulate the pupil. After the camera flash, change in pupil side (e.g., percentage of normal pupil size, pupil latency (i.e., the duration between flash and the onset of pupil response), and pupil constriction rate (i.e., time it takes for the pupil to fully respond to the flash)).

The accommodation rate test has a fixed stimulus and the subject is asked to shift their focus back and forth between two fixed points as fast as they can. The two primary metrics are number of accommodations (i.e., the number of refixations the subject can accomplish in thirty seconds compared to a baseline) and accommodation interval (i.e., the duration required for accommodation of the stimulus).

Probability Values

The probability values 1206 indicative of a disruption in the normal function of the brain correspond with the metrics 1204 and the types of tests 1202. The probability values 1206 include minor traumatic brain injury ("mTBI" on the table 1200), opioid use, marijuana use, intoxication ("INTOX" on the table 1200), Parkinson's ("PARK" on the table 1200), and Alzheimer's ("ALZ" on the table 1200).

For example, the mere presence of a nystagmus indicates that the subject has an 80% change of being intoxicated, and/or a 30% change of having a minor traumatic brain injury. However, the probability values 1206 in table 1200 are based off of averages or other values which may vary based on an individual or a population, which are subject to change and therefore are by no means limiting.

Situational Factors

In addition to the table 1200, situational factors can lead to further understanding and potential identification of disruptions in the normal function of the brain. For example, at a football game, if a player sustained a large impact to their head, assessment of mTBI will be more logical than assessment for opioid use even if both result in a "high confidence" due to overlapping of pertinent measures. By combining measures and situational factors (e.g., environmental factors or test subject specific data that is independent of the captured video or filtered movement data), diagnostic confidence can be achieved. Further, situational factors specific to a test subject can be extracted from a user profile or other data source as described in greater detail herein.

Further, multiple tests can be run based on the combination of resultant measures the confidence of each condition being present can be displayed. For example, if tests are run and the results are:

85% chance of Opioid use
76% chance of mTBI
57% chance of Intoxication or Marijuana use
15% chance of Alzheimer's
10% chance of Parkinson's Combining the results with the knowledge that the subject is 32 years old with a visible wound to the head (i.e., the situational factor), a reasonable conclusion that the disruption in brain function is related to mTBI rather than opioid use, even though opioid use scored higher.

Data Storage

With respect to the process 100, there are a variety of modalities that can be used for storing data associated with the process 100 (e.g., raw movement data, filtered movement data, etc.). In various embodiments, data may be stored in a local storage medium, on a remote server (e.g., cloud storage), or a combination thereof. In some instances, especially with sensitive data such as personal health information (i.e., health insurance portability and accountability act ("HIPAA") compliance), the process 100 may comprise extracting data associated with the facial landmark in response to the regimented pattern, and storing the extracted data associated with the facial landmark in response to the regimented pattern in a storage medium without storing the filtered movement data.

One advantage of only storing the facial landmark in response to the regimented pattern is that the data can be used to further augment the process 100 (e.g., learning algorithm) or allow for research of the data without disclosing unique personal identification data.

Ocular Analysis System

Figure 13:
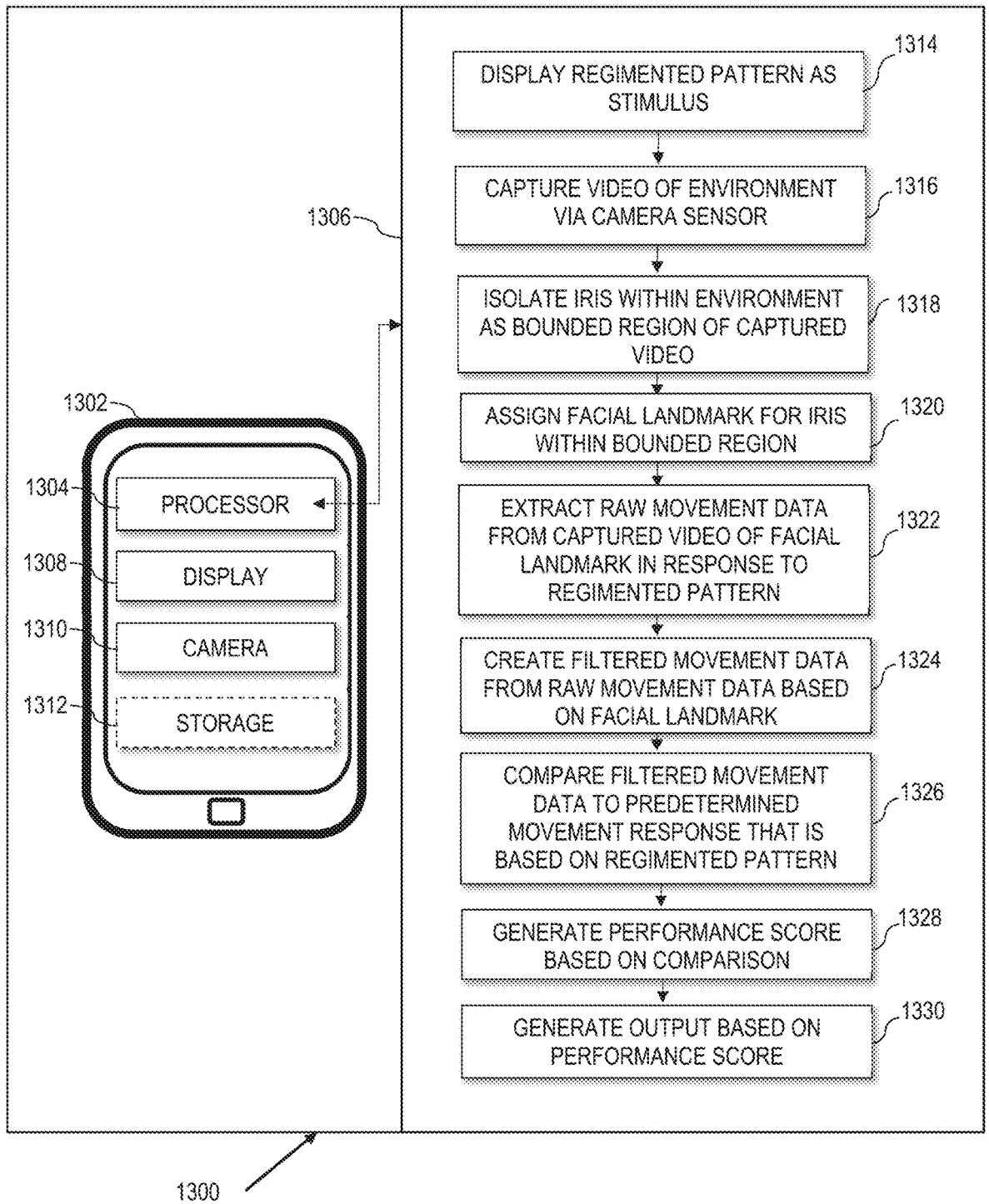
FIG. 13 is an example system for a system for ocular analysis according to various aspects of the present disclosure as described in greater detail herein.

FIG. 13 illustrates an ocular analysis system 1300. Further, all references to FIG. 13 can incorporate the various processes, definitions, and embodiments disclosed in FIGS. 1-12 can be combined in any combination of components described with reference thereto. In this regard, not every disclosed component need be incorporated.

The ocular analysis system 1300 comprises a device 1302, which comprises a processor 1304 coupled to memory 1306, a display 1308, and a camera sensor 1310. In various embodiments, the device 1302 further comprises a storage medium 1312. Moreover, a program in the memory 1306 instructs the processor 1304 to display, at 1314, a regimented pattern as a stimulus on the display 1308.

The program further instructs the processor 1304 to capture, at 1316, video of an environment via the camera sensor 1310. Moreover, the program further instructs the processor 1304 to isolate, at 1318, an iris within the environment as a bounded region of the captured video.

The program also instructs the processor 1304 to assign, at 1320, a facial landmark for an iris within the bounded region. In addition, the program instructs the processor 1304 to extract, at 1322, raw movement data, from the captured video, of the facial landmark in response to the regimented pattern.

Yet further, the program instructs the processor 1304 to create, at 1324, filtered movement data from the raw movement data based on the facial landmark. Moreover, the program instructs the processor 1304 to compare, at 1326, the filtered movement data to a predetermined movement response that is based on the regimented pattern.

In addition, the program instructs the processor 1304 to generate, at 1328, a performance score based on the comparison. The program also instructs the processor 1304 to generate, at 1330, an output based on the performance score.

In various embodiments, the device 1302 is non-fixedly positioned in relation to the face. As noted previously, aspects of the present disclosure allow for compensating or adjusting of a face, head, or facial landmark. Thus, there is no strict requirement that the device 1302 or a subject be at a fixed distance or orientation in relation to one another.

Figure 14:
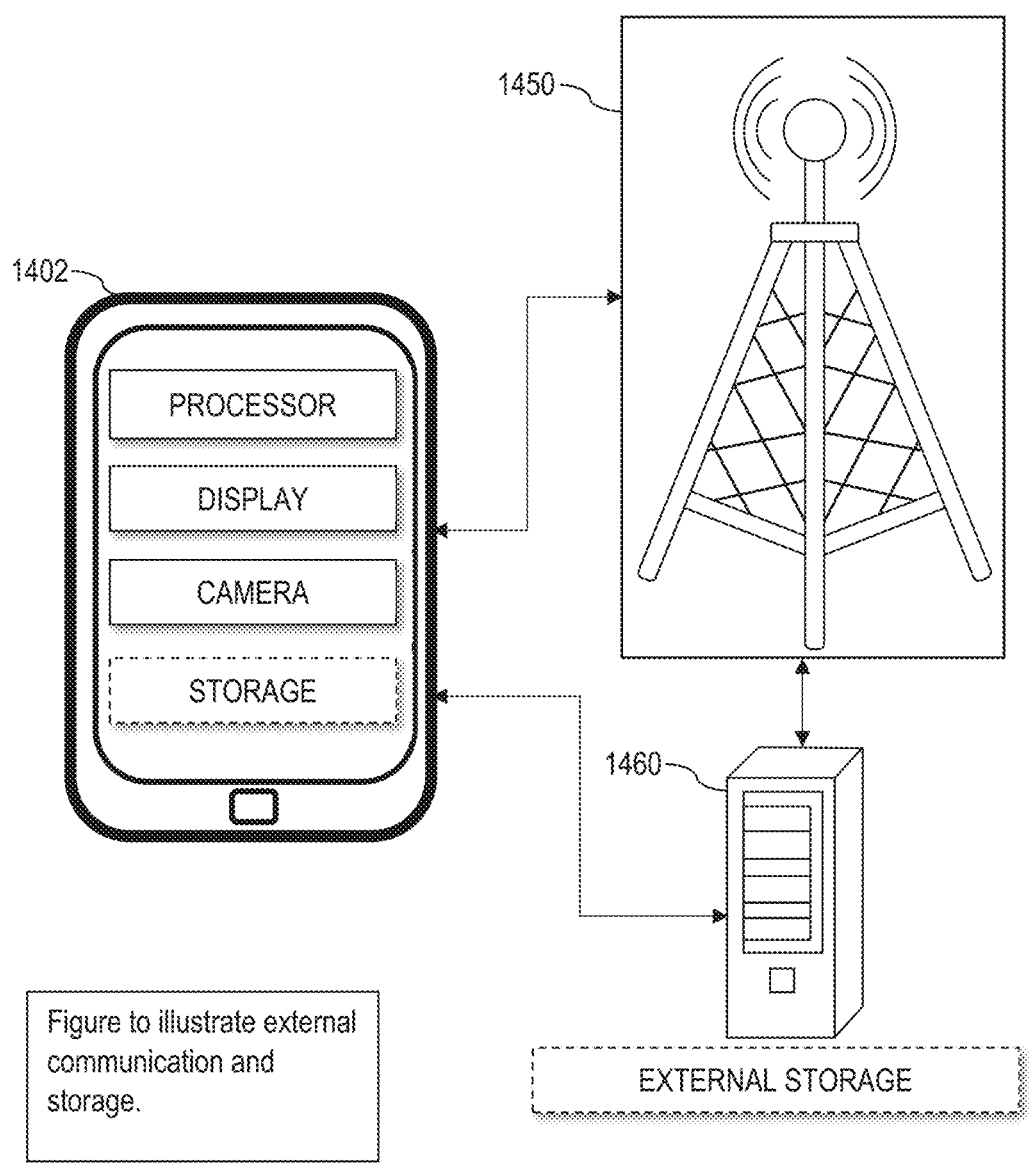
FIG. 14 illustrates external communications for a system for ocular analysis according to various aspects of the present disclosure as described in greater detail herein.

As shown in FIG. 14, the device 1402 may communicate with remote communication devices 1450 (e.g., cellular, satellite, wireless, global positioning system (GPS), etc.) or other external storage 1460 options.

User Profiles and Data

In specific environments (e.g., medical environments) that may use the system 1300, or devices that implement the process 100, it may be necessary from a compliance standpoint (e.g., HIPAA) to require a login or some other form of authentication before the device is activated or useable. Further, transmission of data to and from the device may also require some form of authentication. Authentication also has a benefit of preventing untrained individuals from misuse. However, various implementations of the system and process may be adjusted or streamlined for untrained individuals.

Moreover, the ability to create user profiles also allows users to tweak settings, customized series of tests, or save previously collected base lines as described above.

Some hospitals and organizations use SCAT or a customized "scorecard" in the assessment of cognitive issues. Accordingly, user profiles may be configured so that when a user denotes their affiliation, for example, with a particular hospital network during the registration process, the SCAT Scorecard portion of the testing will be automatically customized to reflect the preferred configurations of that organization. In the even that no organization is entered, or the organization has not specified the content for this section, the standard SCAT tool can be provided by default.

Miscellaneous

Facial landmarks not tied to the iris can be used to correct for movement of a head/face by calculating a rotation matrix representing the rotation and translation of the head with respect to the camera. By removing rotation and translation from the data, and averaging the resulting landmark positions, a stabilized face center can be determined. By relating the position of the detected pupil to this center point, translation and rotation within a 2-D space can be minimized, improving positional quality. A further embodiment involves transforming the landmark points into a 3-D space which can provide more translation and rotation information.

In various embodiments, the systems and processes here may require calibration. During each test in which the range of motion is needed, the subject will be directed to follow a stimulus as it travels to the extremes of the screen. By associating the screen extremes to the extremes of the detected eye rotation a correlation is established.

For example, if the stimulus moves from one side of the screen to the other and the pupil is detected to move 50 pixels, then it can be said that a motion of a pupil by 10 pixels correlates to the subject's gaze shifting by 20% of the total available travel.

Additionally, by comparing the absolute outputs of the pupil location it can be inferred as to what portion of the screen the subject is looking.

Other calibrations or corrections that may be implemented are digital enhancement of the region of interest is performed to enhance the precision and/or accuracy in generating iris landmarks, digital enhancement consists of removing glare from the eye region, digital enhancement consists of contrast correction, and digital enhancement consists of exposure correction.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable storage medium that can direct a computer, other programmable data processing apparatus, or other devices to function in a particular manner, such that the instructions stored in the computer readable storage medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Aspects of the disclosure were chosen and described in order to best explain the principles of the disclosure and the practical application, and to enable others of ordinary skill in the art to understand the disclosure for various embodiments with various modifications as are suited to the particular use contemplated.

What is claimed is:

1. A process for ocular analysis, the process comprising:
    displaying, on a device having a display and a camera sensor, a regimented pattern as a stimulus;
    capturing video of an environment via the camera sensor;
    isolating an iris within the environment as a bounded region of the captured video;
    assigning a facial landmark for the iris within the bounded region;
    extracting raw movement data, from the captured video, of the facial landmark in response to the regimented pattern;
    creating filtered movement data from the raw movement data based on the facial landmark by:
        analyzing the raw movement data by comparing the facial landmark at distinct frames of the captured video;
        determining a variance between the facial landmark at the distinct frames of the captured video;
        identifying a select frame of raw movement data as erroneous data if the variance corresponding to the frame of raw movement data exceeds a predetermined threshold; and
        removing the erroneous data from the raw movement data to create the filtered movement data;
    comparing the filtered movement data to a predetermined movement response that is based on the regimented pattern;
    generating a performance score based on the comparison; and
    generating an output based on the performance score.

2. The process of claim 1, wherein:
    analyzing the movement data by comparing facial landmarks at distinct frames of the captured video comprises identifying a facial landmark that is within the bounded region;
    determining a variance between the facial landmarks at distinct frames of the captured video comprises verifying that the facial landmark is within the bounded region in the distinct frames of the captured video; and
    removing the erroneous movement data from the raw movement data to create the filtered movement data comprises removing the select frame of captured video when the facial landmark is outside the bounded region.

3. The process of claim 1, wherein:
    analyzing the raw movement data by comparing facial landmarks at distinct frames of the captured video comprises calculating a distance between a first targeted facial landmark and a second targeted facial landmark, wherein the targeted facial landmarks are selected within the bounded region;
    determining a variance between the facial landmarks at distinct frames of the captured video comprises determining if the calculated distance between the first targeted facial landmark and the second targeted facial landmark remains consistent at distinct frames of the captured video;
    identifying a select frame of raw movement data as erroneous data comprises determining whether a change in the calculated distance between the first targeted facial landmark and the second targeted facial landmark exceeds a predetermined threshold in the select frame of raw movement data; and
    removing the erroneous data from the raw movement data to create the filtered movement data comprises removing the select frame of captured video if the variance exceeds the predetermined threshold.

4. The process of claim 1, wherein:
    analyzing the raw movement data comprises selecting a set of facial landmarks wherein the set of facial landmarks includes the facial landmark corresponding to the iris;

determining a variance between facial landmarks at distinct frames of the captured video comprises comparing characteristics of the set of facial landmarks at a select frame of the distinct frames of the captured video;

identifying a select frame of raw movement data as erroneous data comprises determining whether the characteristics of the set of facial landmarks exceed a predetermined threshold in the select frame of raw movement data; and removing the erroneous data from the raw movement data to create the filtered movement data comprises removing the select frame of raw movement data wherein the characteristics of the set of facial landmarks exceed the predetermined threshold.

5. A process for ocular analysis, the process comprising:

displaying, on a device having a display and a camera sensor, a regimented pattern as a stimulus by displaying a series of tests as the regimented pattern; and capturing video of an environment via the camera sensor;

isolating an iris within the environment as a bounded region of the captured video;

assigning a facial landmark for the iris within the bounded region;

extracting raw movement data, from the captured video, of the facial landmark in response to the regimented pattern;

creating filtered movement data from the raw movement data based on the facial landmark;

comparing the filtered movement data to a predetermined movement response that is based on the regimented pattern;

generating a performance score based on the comparison by:

generating a current test score for a select test in the series of regimented patterns after the select test is displayed; and combining, after the current test score is generated, the current test score with a combined test score;

ending the displaying of the series of tests when a change in the combined test score when the current test score is incorporated with the combined test score is below a predetermined threshold; and ending the displaying of the series of tests after a predetermined number of tests are displayed, if the displaying of the series of tests does not end because the combined test score when the current test score is incorporated with the combined test score is below a predetermined threshold; and generating an output based on the performance score.

6. The process of claim 1, wherein comparing the filtered movement data to a predetermined movement response that is based on the regimented pattern further comprises:

comparing the filtered movement data and the predetermined movement response that is based on the regimented pattern against at least select one of: a previously collected base line of the filtered movement data, and a test population data of collected filtered movement data.

7. The process of claim 1, wherein assigning a facial landmark further comprises assigning a reference point within the bounded region.

8. The process of claim 1 further comprising storing the raw movement data in a storage medium.

9. The process of claim 1, wherein:

comparing the filtered movement data to a predetermined movement response that is based on the regimented pattern comprises:

extracting data values filtered movement data and the predetermined movement response that is based on the regimented pattern; and comparing the extracted data values against known data values associated with a disruption in the normal function of the brain; and generating a performance score based on the comparison comprises: generating a performance score based upon the compared extracted data values with the known data values associated with a disruption in the normal function of the brain.

10. A process for ocular analysis, the process comprising:

displaying, on a device having a display and a camera sensor, a regimented pattern as a stimulus;

capturing video of an environment via the camera sensor;

isolating an iris within the environment as a bounded region of the captured video;

assigning a facial landmark for the iris within the bounded region;

extracting raw movement data, from the captured video, of the facial landmark in response to the regimented pattern;

creating filtered movement data from the raw movement data based on the facial landmark;

comparing the filtered movement data to a predetermined movement response that is based on the regimented pattern;

generating a performance score based on the comparison;

generating an output based on the performance score;

extracting data associated with the facial landmark in response to the regimented pattern; and storing the extracted data associated with the facial landmark in response to the regimented pattern in a storage medium without storing the filtered movement data.

* * * * *